US00PP18904P2

(12) United States Plant Patent
Core

(10) Patent No.: US PP18,904 P2
(45) Date of Patent: Jun. 10, 2008

(54) ***NEPETA* PLANT NAMED 'PSFIKE'**

(50) Latin Name: *Nepeta*
Varietal Denomination: Psfike

(75) Inventor: Brian Core, Brighton, CO (US)

(73) Assignee: Plant Select, Fort Collins, CO (US)

( * ) Notice: Subject to any disclaimer, the term of this patent is extended or adjusted under 35 U.S.C. 154(b) by 17 days.

(21) Appl. No.: 11/699,706

(22) Filed: Jan. 30, 2007

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—Jondle & Associates, P.C.

(57) ABSTRACT

A new *nepeta* plant particularly distinguished by a low, spreading plant habit, floriferous with numerous purple-violet flowers, a long blooming period, mint-fragranced foliage and exceptional garden performance, is disclosed.

3 Drawing Sheets

Genus and species: *Nepeta* sp.
Variety denomination: 'Psfike'.

BACKGROUND OF THE NEW PLANT

The present invention comprises a new and distinct cultivar of *Nepeta,* botanically known as *Nepeta* sp. and hereinafter referred to by the cultivar name 'Psfike'. The new hybrid originated from an open-pollination cross between an individual plant of *Nepeta amethystina* var. *laciniata* (unpatented) as the seed parent, having bluish-violet flowers and an unknown individual plant of *Nepeta* sp. (unpatented) as the pollen parent.

Seedlings of this hybrid were grown from seed that was collected from a specimen of *Nepeta amethystina* var. *laciniata* that was growing in Denver, Colo. This new *Nepeta* hybrid was selected as a single plant in April 2004 from this group of seedlings that were grown in Brighton, Colo. The present invention has been asexually reproduced by cuttings in a controlled environment in Brighton, Colo. since July 2004. The present invention has been found to retain its distinctive characteristics through successive asexual propagations.

SUMMARY OF THE INVENTION

The following are the most outstanding and distinguishing characteristics of the present invention when grown under normal horticultural practices in Brighton, Colo.:

1. A low, spreading plant habit.
2. Floriferous nature;
3. A long blooming period;
4. Foliage that is mint-fragranced; and
5. Exceptional garden performance.

DESCRIPTION OF THE PHOTOGRAPHS

This new *nepeta* plant is illustrated by the accompanying photographs which show overall plant habit including blooms, buds, and foliage of the plant; the colors shown are as true as can be reasonably obtained by conventional photographic procedures. The photographs are of a two-year old plant grown in Brighton, Colo.

DESCRIPTION OF THE NEW PLANT

Figure 1:
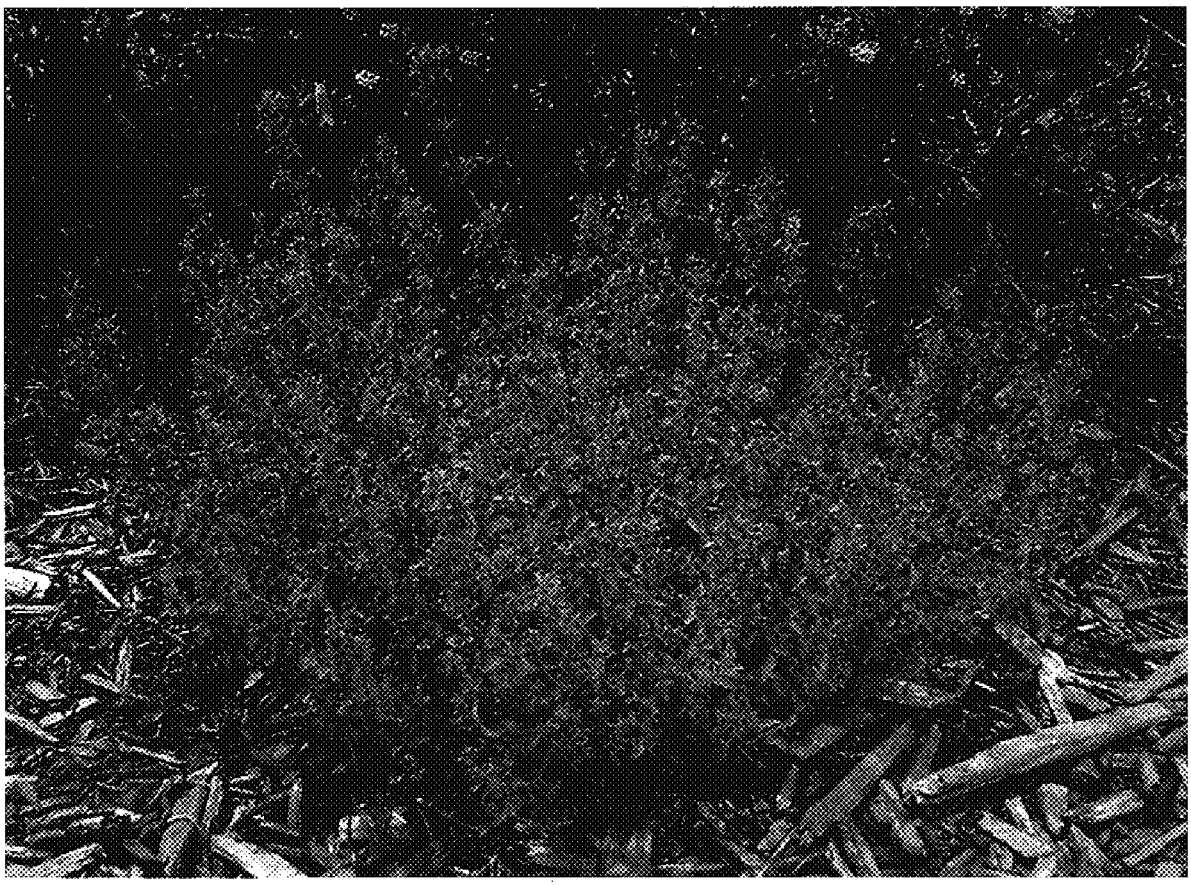
FIG. 1 shows the overall plant habit, including blooms, buds, mature foliage, and plant habit of a plant growing outdoors.
Figure 2:
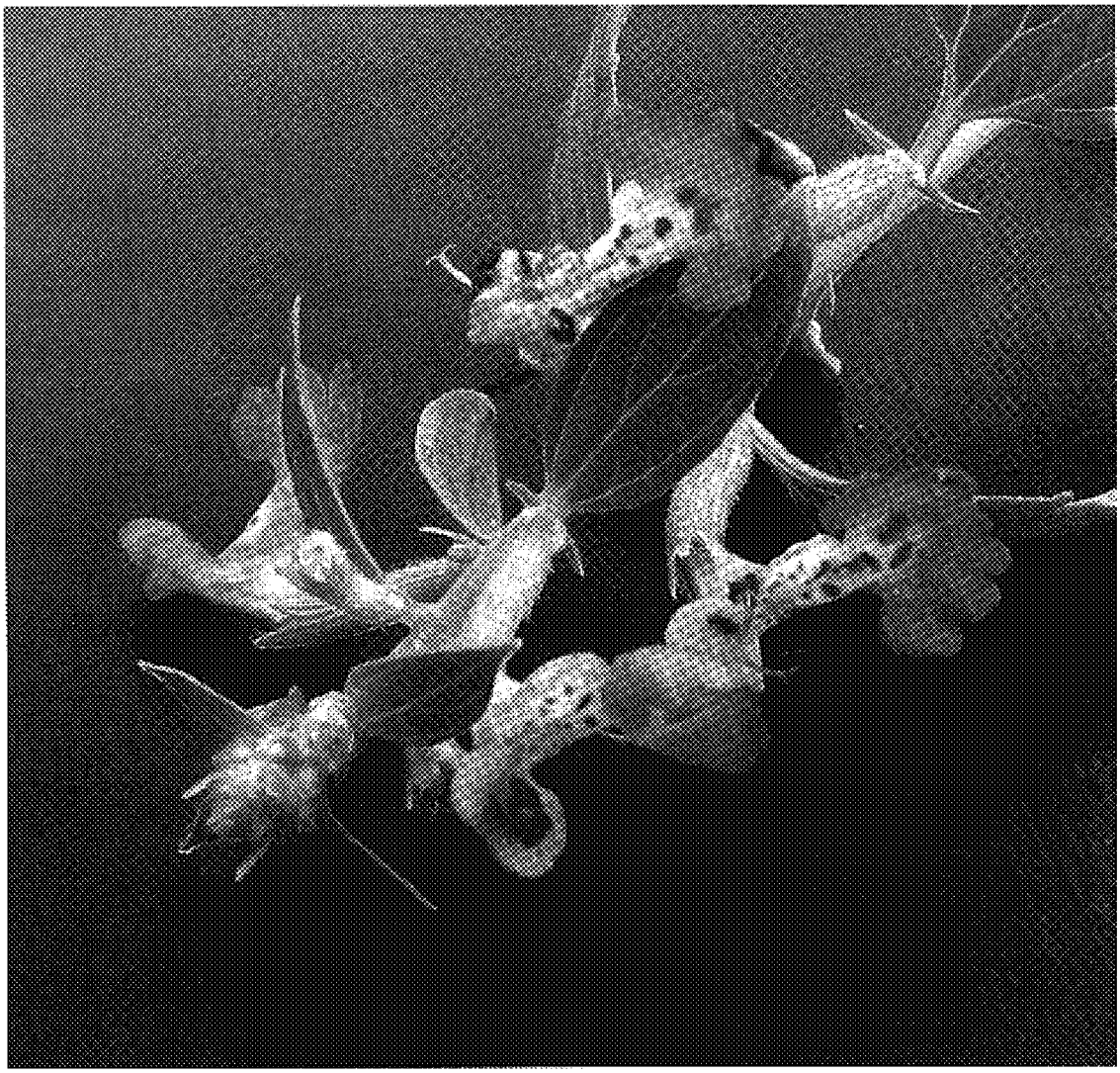
FIG. 2 shows a close-up of the mature inflorescence of a greenhouse-grown plant.
Figure 3:
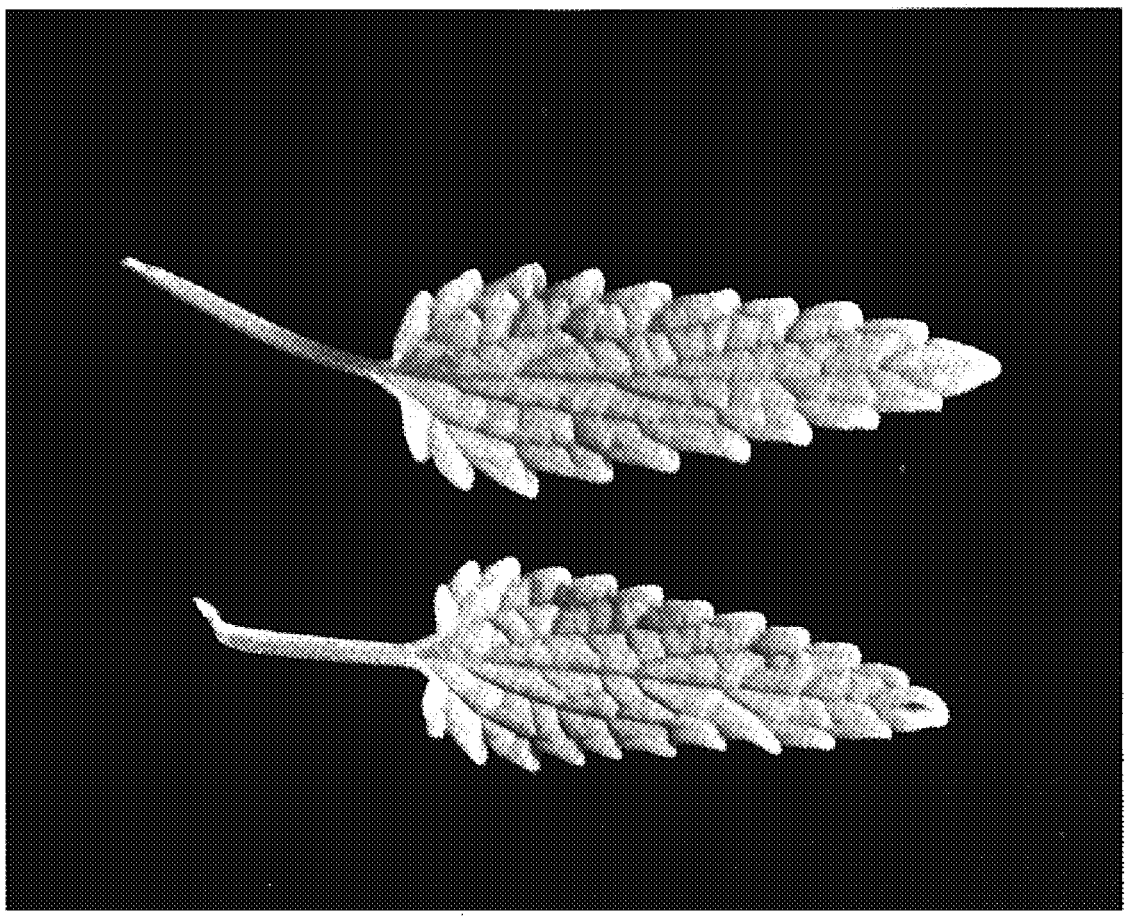
FIG. 3 shows a close-up of two mature leaves from a greenhouse-grown plant.

The following detailed description sets forth the distinctive characteristics of 'Psfike'. The data which define these characteristics were collected from asexual reproductions carried out in Brighton, Colo. The plant history was taken on 14-month old plants grown in a greenhouse in late fall. Observations of form, habit, height and width were made in the early fall from garden-grown plants in situ. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family.*—Labiatae.
- *Botanical.*—*Nepeta* sp.
- *Common name.*—Catmint.

Parentage:
- *Female parent.*—An individual plant of *Nepeta amethystina* var. *laciniata* (unpatented) having bluish-violet flowers.
- *Male parent.*—An unknown individual plant of *Nepeta* sp. (unpatented).

Plant:
- *Form.*—Herbaceious perennial.
- *Habit.*—Spreading.
- *Height (from top of soil) in cm.*—20 cm (non-blooming plant). 30 cm (to top of inflorescence).
- *Width (horizontal plant diameter).*—75 cm.
- *Propagation.*—By terminal cuttings.
- *Time to produce a finished flowering plant.*—90 to 120 days.
- *Time to initiate and develop roots.*—8 days at 21° C. in the summer. 12 days at 21° C. in the winter.
- *Root description.*—Fine, freely branching.

Stems: (square in cross-section).
*Average number per plant.*—130.
*Diameter.*—0.15 cm.
*Internode length.*—1.2 cm.
*Color.*—R.H.S. 145C (yellow-green).
*Anthocyanin.*—Absent.
*Texture.*—Short pubescence.

Leaves:
*Arrangement.*—Opposite, simple.
*Size.*—Length: 1.5 cm. Width: 0.9 cm.
*Shape.*—Deltoid-cordate.
*Apex.*—Acute.
*Base.*—Cordate to truncate.
*Margin.*—Crenate.
*Texture.*—Rugose.
*Fragrance.*—Aromatic, pungent with a trace of mint.
*Immature leaf.*—Color: Upper surface: RHS 138B (green). Lower surface: RHS 138C (green).
*Mature leaf.*—Color: Upper surface: Close to RHS 147B (yellow-green), but darker. Lower surface: Close to RHS 147C (yellow-green), but brighter.
*Venation pattern.*—Longitudinal.
*Venation color.*—Upper surface: Close to RHS 147B (yellow-green), but darker. Lower surface: Close to RHS 147C (yellow-green), but brighter.
*Petioles.*—Length: 0.8 cm. Diameter: 0.1 cm. Texture: Short pubescence. Color: Upper surface: Close to RHS 147B (yellow-green), but darker. Lower surface: Close to RHS 147C (yellow-green), but brighter.

Flower bud:
*Shape.*—Ovoid.
*Color at tight bud.*—RHS 147D (yellow-green) at the proximal end changing to RHS 143C (yellow-green) at the distal end.
*Size.*—Length: 0.2 cm. Diameter: 0.1 cm.

Flower description:
*Blooming habit* (*flowering season*).—April to October in the Denver, Colo. area.
*Flower type and arrangement.*—Elongate racemes with axially cymes subtended by leafy bracts.
*Lastingness of the individual blooms on the plant.*—About one week.
*Fragrance.*—None noted.
*Pedicels.*—Color: RHS 139D (yellow-green). Length: 0.2 cm. Diameter: 0.075 cm. Texture: Short pubescence. Aspect: About 45° to rachis.

Flowers:
*Shape.*—Zygomorphic, bilabiate.
*Size.*—Diameter (flower face): 0.7 cm. Depth (total length of flower): 1.1 cm.
*Funnel* (*corolla*).—Length: 0.9 cm. Diameter (at opening): 0.1 cm. Outside texture: Short pubescence. Color inside (throat): Opening is RHS 155A (pure white) with spots colored RHS 72A (red-purple) and aging to RHS N81D (purple-violet) with RHS 72A (red-purple) spots. Color outside: RHS N18D (purple-violet).
*Mature flower.*—Face/Margin color: Upper surface: RHS N82A (purple-violet). Lower surface: RHS N82A (purple-violet).
*Petals.*—Arrangement: Bilabiate, 5-petaled, with 2 fused petals on upper lip, 3 fused petals on lower lip, and all 5 petals fused at base to form a funnel-shaped structure.
*Apex.*—Each individual petal in upper and lower lip has a rounded apex.
*Base.*—Each individual petal in upper and lower lip has a fused base.
*Margin.*—Each individual petal in upper and lower lip has an entire margin.
*Texture.*—Both the upper and lower lips are glabrous.
*Length.*—Upper lip: 0.3 cm. Lower lip: 0.4 cm.
*Width.*—Upper lip: 0.7 cm. Lower lip: 0.4 cm.

Sepals:
*Number and arrangement.*—5 petals fused to form a calyx tube.
*Color.*—When opening: Upper surface: RHS 145B (yellow-green). Lower surface: RHS 147C (yellow-green) at the distal end and fading to RHS 148C at the proximal end. Fully opened: Upper surface: RHS 145B (yellow-green). Lower surface: RHS 138B (green) and overlaid with RHS N82A (purple-violet).
*Length.*—0.7 cm.
*Width.*—0.15 cm.
*Shape.*—Tubular.
*Apex.*—Acute.
*Base.*—Fused.
*Margin.*—Entire.
*Texture.*—Short pubescence.

Flower bracts:
*Quantity per verticillastic.*—1.
*Length.*—1.2 cm.
*Width.*—0.4 cm.
*Shape.*—Lanceolate.
*Apex.*—Acuminate.
*Texture.*—Short pubescence.
*Color.*—Upper surface: RHS 137B (green). Lower surface: RHS 138B (green).

Peduncle:
*Length.*—5.0 cm.
*Diameter.*—0.1 cm.
*Color.*—RHS 138B (green).
*Aspect.*—Erect.

Reproductive organs:
*Stamens.*—Quantity (per flower): 4. Shape: Inserted. Color: RHS 76A (purple). Filament length: 0.5 cm. Filament diameter: 0.0125 cm.
*Anther.*—Shape: Bi-lobed. Color: RHS 83A (violet). Length: 0.08 cm. Diameter: 0.02 cm.
*Pollen.*—Amount and color: None observed and more believed to be present.
*Pistils.*—Quantity (per flower): 1. Length: 1.1 cm. Diameter: 0.02 cm.
*Stigma.*—Shape: Bifid (forked). Color: RHS 81C (purple-violet). Length: 0.02 cm.
*Style.*—Shape: Erect. Color: RHS 75C (purple). Length: 0.9 cm. Diameter: 0.02 cm. Ovary color: RHS 75C (purple).

Fruit and seed set: None observed.

Disease and insect resistance: Insect and disease resistance is believed to be typical for the genus. *Nepeta* are reputed to be deer-resistant plants.

COMPARISON WITH PARENTAL AND COMMERCIAL CULTIVARS

'Psfike' differs from the female parent, an individual plant of *Nepeta amethystina* var. *laciniata* (unpatented) having bluish-violet flowers in that 'Psfike' has darker violet-purple flowers than the female parent. Additionally, the leaf margins of 'Psfike' are crenate, while the leaf margins of the female parent are dentate.

The male parent of 'Psfike' is unknown and thus, a comparison between 'Psfike' and the male cannot be made.

'Psfike' differs from individual plants of *Nepeta×faassenii,* a commonly cultivated and unpatented hybrid plant in that 'Psfike' has shorter internodes, has a more compact plant habit and has a longer blooming period than individual plants of *Nepeta×faassenii.* Additionally, 'Psfike' has finer foliage texture, smaller leaves that are more yellow-green in color and more sparsely pubescent and foliage that has a mint fragrance, while individual plants of *Nepeta×faassenii* have foliage that does not typically have a mint fragrance (i.e., is rank in odor) and is more gray-green and densely pubescent.

I claim:

1. A new and distinct cultivar of *nepeta* plant as shown and described herein.

* * * * *